United States Patent [19]

Easterbrook

[11] 4,031,214
[45] June 21, 1977

[54] SULPHONAMIDE AND 2,4-DIAMINOPYRIMIDINE INJECTABLE SUSPENSION

[75] Inventor: Michael George Easterbrook, Meopham, England

[73] Assignee: Burroughs Wellcome Co., Research Triangle Park, N.C.

[22] Filed: Apr. 7, 1975

[21] Appl. No.: 565,964

Related U.S. Application Data

[63] Continuation of Ser. No. 123,079, March 10, 1971, abandoned.

[30] Foreign Application Priority Data

Mar. 13, 1970 United Kingdom ............. 12348/70

[52] U.S. Cl. ............................... 424/229; 424/228; 424/251

[51] Int. Cl.$^2$ ............... A61K 31/63; A61K 31/635; A61K 31/505

[58] Field of Search .................... 424/229, 228, 251

[56] References Cited

UNITED STATES PATENTS 3,551,564   12/1970   Klaui et al. ........................ 424/229
3,728,452   4/1973    Haber et al. ....................... 424/229

*Primary Examiner*—Sam Rosen
*Attorney, Agent, or Firm*—Donald Brown

[57] ABSTRACT

An injectable suspension of a sulphonamide/2,4-diaminopyrimidine combination formed utilizing a strong base and basic pH conditions which is suitable for the treatment of bacterial infections in mammals or birds.

17 Claims, No Drawings

SULPHONAMIDE AND 2,4-DIAMINOPYRIMIDINE INJECTABLE SUSPENSION

This is a continuation of application Ser. No. 123079, filed on Mar. 10, 1971 now abandoned.

The present invention relates to injectable therapeutic compositions.

It is well known that the chemotherapeutic, especially the antibacterial, activities of the sulphonamides and of certain 2,4-diaminopyrimidines are mutually enhanced when these agents are acting together. Although the enhancement is mutual, these 2,4-diaminopyrimidines are hereinafter referred to as potentiators.

2,4-Diaminopyrimidines and methods of synthesis thereof are described, for example, in British Patent Specifications Nos. 715 813; 734 801; 875 562; 957 797; and 1 128 234; the specification of British Patent Application No 5246/68 and the specification of South African Application No. 65/5618.

An important class of such potentiators are 2,4-diaminopyrimidines carrying a substituted benzyl group in the 5-position, or a substituted phenyl group in the 5-position together with a lower alkyl group in the 6-position. As specific compounds of value there may be mentioned trimethoprim 2,4-diamino-5-(3,4,5-trimethoxybenzyl)pyrimidine , diaveridine 2,4-diamino-5-(3,4-dimethoxybenzyl)pyrimidine , 2,4-diamino-5-(3,4,6-trimethoxybenzyl)pyrimidine, 2,4-diamino-5-(4-chlorobenzyl)-6-ethylpyrimidine, ormetoprim 2,4-diamino-5-(2-methyl-4,5-dimethoxybenzyl)pyrimidine , 2,4-diamino-5-(3,4-dimethoxy-5-bromobenzyl)pyrimidine, and pyrimethamine 2,4-diamino-5-(4-chlorophenyl)-6-ethylpyrimidine .

All these compounds are known to have valuable chemotherapeutic activity and to be potentiators of sulphonamides in the sense referred to above.

A preferred class of potentiators for use in the present invention is that of formula:

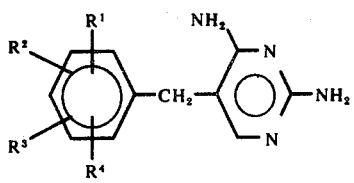

Where $R^1$, $R^2$, $R^3$ and $R^4$ are the same or different and can each be a hydrogen atom, a halogen atom, an alkyl group, an alkoxy group or a benzyloxy group or when $R^1$ and $R^2$ are each hydrogen atoms $R^3$ and $R^4$ taken together can be a methylene dioxy group.

As examples of sulphonamides, the action of which is capable of being thus potentiated, there may be mentioned sulphadiazine { 2-(4-aminobenzenesulphonamido)pyrimidine}, sulfadoxine {4-(4-aminobenzenesulphonamido)-5,6-dimethoxypyrimidine}, sulphadimethoxine {4-(4-aminobenzenesulphonamide)-2,6-dimethoxypyrimidine, sulphamethoxazole}{3-(4-aminobenzenesulphonamido)-5-methylisoxazole}, sulphquinoxaline {2-sulphonamido-quinoxaline}, and sulphadimidine {2-(4-aminobenzenesulphonamido)-4,6-dimethylpyrimidine}.

A preferred class of sulphonamides for use in the present invention is that of formula:

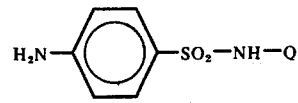

Wherein Q is a substituted or unsubstituted pyrimidin-2-yl or -4-yl group or a substituted isoxazolyl group.

Usually the ratio of sulphonamide to potentiator for useful therapeutic effect is of the order of 5:1 (w/w) with a preferred ratio lying between 10:1 and 2:1, (w/w) although in certain cases it may be found desirable to have a ratio of as high as 20:1 (w/w), or as low as 0.5:1 or even 0.1:1.

While such preparations are frequently administered orally, there is also a need for injectable preparations. However, there arises a problem in preparing an injectable composition containing both a sulphonamide and a basically reacting sulphonamide-potentiator because of the particular solubility properties of both components. Sulphonamides only form suitable soluble salts with certain bases whilst basically reacting sulphonamide-potentiators only give suitable soluble salts with certain acids. Mixing of aqueous and other pharmaceutically acceptable ionic solutions of both components results in precipitation, which makes the manufacture of injectable solutions in this way impossible.

Proposals have been made for formulating sulphonamide and potentiator mixtures with various solvents other than water, but such preparations all suffer from the well known disadvantages of injection preparations in which a substantial part of the carrier liquid is nonaqueous.

Another disadvantage of known sulphonamide/-potentiator preparations which are in the form of solutions is that it is not possible to increase the concentrations of the active ingredients in the solution without increasing the viscosity of the solution which increase in viscosity may render the solution undesirable for injection purposes.

The present invention is based, in part, on the discovery that high concentrations of the potentiator can be obtained in an aqueous injectable preparation without attendant undesirably high viscosity of the preparation if the potentiator is present in the form of finely divided particles suspended in an aqueous solution of a salt of a sulphonamide with a strong base.

Initial attempts to form such a preparation were unsuccessful because of the unexpected formation of an equimolar complex between the sulphonamide and the potentiator, which complex formed crystals in the injectable preparation.

Crystallization:

a. caused fluctuation in the concentrations of the contents of the liquid and solid phases, which introduced uncertainty in use, since the absorption of these phases by the mammal or bird proceeds at a different rate, b. was found to be dependent on time so that various amounts of equimolar complex were found to be present as crystals of random size in samples of differing ages, and c. created crystals of random size which occasionally acted as seeds for further crystallization. The suspensions of such solid phases showed a variety of physical properties, e.g. viscosity, which involved different reactions at the site of administration of the injectable preparation. Crystalline growth of the 1-1 complex completely upsets the particle size distribution of the preparation making it unusable for injection purposes.

On further investigation, the applicants discovered that if the pH of the preparation was raised to a level at which the potentiator was substantially unionized the small amount of equimolar complex which was formed, if any, was not sufficient to exceed the solubility thereof in the sulphonamide solution and, therefore, crystalline growth of the complex did not occur.

It is an object of the present invention to provide an injectable preparation of a sulphonamide and a potentiator therefor in which the liquid vehicle consists mainly of water. The present invention is concerned with preparations which are aqueous and are termed hereinafter "injectable aqueous preparations." The presence of organic solvents for example alcohol, glycerol and propylene glycol is not excluded, but their presence is not advantageous and may disturb the stability of the preparation by their solubilizing action.

Accordingly, pharmaceutically present invention provides an aqueous injectable preparation, as herein defined, which comprises a suspension of a finely divided potentiator, as herein defined, substantially all of the particles of potentiator in the suspension having a largest dimension less than $50 \mu\mu$m, in an aqueous solution of a pharmaceuticaly acceptable water soluble salt of a sulphonamide with a strong base.

By the term "potentiator" as used herein there is meant all 2,4-diamino pyrimidines which are active against bacterial infections of mammals or birds and which are not substituted by groups such as the hydroxy group attached to an aromatic nucleus which will react with the base from which the salt of the sulphonamide is derived.

Under the above basic conditions the potentiator is present in the suspension almost completely in the form of the free base, i.e. the unionised form. Depending on the relative solubility of equimolar complex as compared with the solubility of the potentiator itself, the formation of such equimolar complexes can be envisaged. However, such formation can be prevented by increasing the pH of the suspension. The potentiator is usually only ionised to a very small extent, and suitably stable compositions according to the invention have been obtained, above a pH of 9.75. The pH of the preparation will normally be at least 10 and preferably will lie in the range from 10 to 10.5. The upper limit of pH is not critical and is determined by factors well known to those skilled in the art such as tolerance of the animal to be injected to the injectable solution. In general, it is undesirable to use a suspension having a pH greater than 12 in view of the irritation caused to the animal or bird to be injected.

In another aspect of the invention there is provided a method of treating bacterial infections in birds or mammals other than human beings which comprises injecting either intramuscularly or subcutaneously, an effective dosage of the injectable preparation of the invention.

It has been surprisingly found that, though one of the components (namely the sulphonamide) is in solution and the other is in the solid state, the efficacy of the peparation is in no way impaired, and that by the present invention, an effective injectable aqueous preparation of sulphonamide and sulphonamide-potentiator may be readily prepared.

An important and critical feature of the present invention lies in the degree of subdivision of the suspended sulphonamide-potentiator. The degree of subdivision where substantially all of the particles, i.e. at least 99% by number of the particles, have a largest dimension of $50\mu$m is as large as can be tolerated. Normally, all of the particles will have a largest dimension less than $50\mu$m. It has been found that the object of the invention can be very successfully achieved if the degree of subdivision is such that 99.5% by number have a largest dimension less that 5 microns. However, useful results are obtained if the particles are larger than this; for example it is adequate if 95% by number of the particles have a largest dimension of less than 5 microns. Preferably, 90% by number of the potentiator particles have a maximum dimension of less than $20\mu$m, more preferably 95% by number of the particles have a maximum dimension of less than $20\mu$m, most preferably 99.5% by number of the particles have a maximum dimension of less than $20\mu$m. It will be readily understood that adequate degrees of subdivision for any particular formulation envisaged can readily be determined by simple experiment using well-known and standard techniques.

As mentioned previously, the pH of the preparation is of paramount importance in view of the undesirable formation of crystals of the complex of potentiator and sulphonamide which may be observed at certain pH ranges.

The nature of the injectable preparation is such that it is not recommended for intravenous injections, unless all of the particles have a largest dimension less than $10\mu$m.

One advantage of the preparation according to the invention is that a considerably larger quantity of medicament may be incorporated into a given volume of preparation than has been possible with formulations hitherto proposed for the same purpose. By the invention, a composition can be produced which has a high concentration of active ingredients and can at the same time have a viscosity low enough for it to be readily injected. This is a particularly valuable advantage in veterinary medicine when it is desired to inject larger animals such as horses or cattle, as otherwise undesirably large volumes of liquid are required. It is found that preparations may be prepared in which even up to 70% w/v (weight in volume, i.e. weight of component per unit volume of formulation) of the formulation consists of medicament; usually the practical upper limit is determined by the viscosity of the preparation which must not be too high to impede injection through the syringe and needle. However, more viscous preparations may be diluted immediately before use. It is remarkable that, the preparations of the invention, notwithstanding the fact that they are suspensions, also provide a most convenient means of dispensing the medicaments for administration orally by dilution in drinking water.

As already mentioned, the sulphonamide is present as the salt of a strong base; suitable substances which can act as the base are alkali metal hydroxides such as sodium hydroxide. With certain sulphonamides it is possible to use certain organic bases such as monoethanolamine, diethanolamine and trimethanolamine and it is to be understood that such bases are embraced for the purposes of the invention, within the term "strong Base".

Again the suitability of a base for any particular sulphonamide can be readily found by simple testing and experiment. The strong base must be sufficiently strong to react with the sulphonamide and produce a final pH which is high enough to render the potentiator sufficiently unionised that the amount of equimolar complex formed, if any, is not sufficient to exceed the solubility of the equimolar complex in the sulphonamide solution. Extra base may be added, over and above that required for reaction with the sulphonamide, to produce the necessary high pH.

It is usually found that the presence of wetting agent, which is normally a non-ionic wetting agent, since they are not generally toxic, assists in the stability of the formulation. As a suitable wetting agent there may be mentioned polyoxyethylene monooleate. Use of anionic or cationic wetting agents is generally to be avoided since they are usually toxic. Also flocculating agents, e.g. sodium citrate, may be incorporated if desired.

It is usually convenient to prepare the compositions of the invention by an aseptic ball-milling of the sterile potentiator in a sterile solution of the appropriate salt, for example the sodium salt, of the sulphonamide. Alternatively sterile finely divided potentiator may be dispersed in a sterile solution of the appropriate salt of the sulphonamide using a simple mixing technique. The solution of the sulphonamide may be sterilised by conventional methods such as heating or filtration. The potentiator may be sterilised as a solid by heating or irradiation or prepared sterile.

In this manner preparations containing 40% w/v sulfadoxine and 8% w/v trimethoprim can readily be prepared and even higher concentrations, for example up to 70% w/v sulfadoxine and 14% w/v trimethoprim, are possible though at this highest concentration the preparation is too viscous for satisfactory injection without previous dilution. Similarly a preparation containing 20% sulphadiazine and 4% w/v trimethoprim can be prepared. The sulphonamide sulphamethoxazole can also be used in a similar manner with trimethoprim.

To achieve a preparation with maximum stability and having a long shelf life it is desirable that the potentiator should have a solubility in the basic solution of the sulphonamide of less than 0.5% w/v. The higher the solubility of the suspended potentiator, the more readily there takes place a mass transfer between the phases which gives rise to crystal growth, as a result of which the physical characteristics of the suspension as prepared become altered adversely. However the invention is not limited to use with potentiators having a solubility less than 0.5%, as therapeutically useful preparations, though with a somewhat lessened stability, may be prepared if the potentiator has a higher solubility than this. The solubility of any selected potentiator may be readily be determined by standard methods.

The invention will now be described with reference to the accompanying examples.

Example 1

| The following ingredients were used: | |
|---|---|
| Sulfadoxine | 4080.0 grams |
| Trimethoprim | 816.0 grams |
| Polyoxyethylene Sorbitan mono-oleate | 2.0 grams |
| Diethanolamine | 60.0 grams |
| Sodium hydroxide | 500.0 grams |
| 30% Sodium hydroxide solution | q.s. |
| Water for Injection | to 10,000.0 ml. |

The sulfadoxine is dispersed in about half the final volume of the water for injection. The sodium hydroxide and diethanolamine are dissolved in about one tenth of the final volume of water and this solution is added to the dispersion of sulphadoxine. With continuous stirring sufficient of the 30% sodium hydroxide solution is added to dissolve the sulphadoxine and to give a final pH of 10.0 to 10.3. The polyoxyethylene sorbitan mono-oleate is then added, the mixture filtered and sterilized at 115° C for 30 minutes.

The trimethoprim is sterilised by heating at 150° C for one hour in a hot air oven, and is added with the above mentioned solution under aseptic conditions to a sterilised porcelain ball mill and milled until the majority of particles are below 5 microns, (99% by number have a maximum dimension of $20\mu$) then filled into 50 ml vials under aseptic conditions.

The above described preparation was found to be very convenient for use as an antibacterial preparation for intramuscular injection into farm animals, particularly cattle, sheep, pigs and horses. It is preferably not administered intravenously or subcutaneously.

Example 2

| | |
|---|---|
| Sulphadiazine B.P. | 244.80 grams |
| Trimethoprim | 48.96 grams |
| Polyoxyethylene sorbitan mono-oleate | 0.24 grams |
| Diethanolamine | 7.20 grams |
| Sodium hydroxide | 33.00 grams |
| Sodium metabisulphite | 1.20 grams |
| 30% sodium hydroxide solution | q.s. |
| Methylhydroxybenzoate | 1.20 grams |
| Water for Injections | to 1,200.00 ml. |

Half the final volume of water for injection is heated to 90° C and the methylhydroxybenzoate is dissolved in it. The solution is allowed to cool and the sulphadiazine is suspended in it. The diethanolamine and sodium hydroxide are dissolved in one twentieth of the final volume of water for injections and the solution is added to the sulphadiazine suspension. The sodium metabisulphite dissolved in a small quantity of water for injection and the polyoxyethylene sorbitan mono-oleate are then added.

There is then added to the suspension sufficient 30% sodium hydroxide solution to dissolve the sulphadiazine and give a pH in the range of 10.0 to 10.5. The solution is filtered and made to a final volume less than the displacement volume of the trimethoprim. (Assume lg trimethoprim displaces 0.75 ml of vehicle). The solution is then sterilized by heating to 115° C for 30 minutes.

The trimethoprim is sterilized by heating at 150° C for one hour in a hot air oven. The sterilized solution and the sterilized trimethoprim are then milled in a sterilized procelain ball mill until the majority of particles are below 5 microns, 99% less than $20\mu$. The suspension is filled into 20 ml vials under aseptic conditions.

The above described preparation was found to be very convenient for use as an antibacterial preparation for intramuscular or subcutaneous injection in cats. In dogs, subcutaneous injection produced some local irritancy but intramuscular injections were well tolerated.

Example 3

| The following ingredients were used: | |
|---|---|
| Sulphamethoxazole | 20.00 grams |
| Trimethoprim | 4.00 grams |
| Isethionic acid or methanesulpnonic acid | q.s. |

Example 3-continued

| | |
|---|---|
| Sodium hydroxide | q.s. |
| Polyvinylpyrrolidone | 4.00 grams |
| Polyoxyethylene sorbitan mono-oleate | 0.02 grams |
| Water for injection | to 100.00 ml |

The trimethoprim is dispersed in a minimum quantity of water for injection and sufficient isethionic acid or methanesulphonic acid is added to neutralize and dissolve it; the solution is diluted with water for injection to give a solution of approximately 10% (w/v) strength.

The sulphamethoxazole is dispersed in about one fifth of the volume of the water for injection and sufficient sodium hydroxide is added to dissolve it with sufficient excess to precipitate the trimethoprim in the next step and to achieve a final pH in the range from 10 to 10.5. The polyvinylpyrrolidone and the polyoxyethylene sorbitan mono-oleate are then dissolved and under conditions of high speed stirring the trimethoprim solution is added in a region of high turbulence, thus precipitating the trimethoprim base in fine crystalline form (90% by number of the trimethoprim particles had a maximum dimension less than $20\mu$.) The suspension is diluted with water.

The advantage of this method is that all constituents of the formula can be subjected to sterilisation by filtration at the appropriate stages in the procedure given above.

Example 4

| | |
|---|---|
| Diaveridine | 0.64g |
| Sulphaquinoxaline | 2.56g |
| Purified water to | 100ml |
| Sodium Hydroxide | 0.35g |
| 30% Sodium Hydroxide | q.s. |

The solid sodium hydroxide was dissolved in about three quarters of the final volume of purified water. The sulphaquinoxaline was then added and dissolved up using mechanical stirring and, if necessary, heating up to 40° C. The solution was then filtered through a No. 3 sintered glass filter and made up to volume, less the displacement volume of diaveridine, with purified water added through the filter.

The diaveridine was milled with a portion of the sulphaquinoxaline solution using a porcelain ball mill until 90% of the particles had a largest diameter which was less than $5\mu m$.

The mill was then emptied and the suspension was diluted with the remaining sulphaquinoxaline solution. Sufficient 30% sodium hydroxide was added to achieve a final pH for the suspension of 10.0.

What is claimed is:

1. An aqueous injectable preparation which comprises a suspension of a finely divided potentiator of the formula

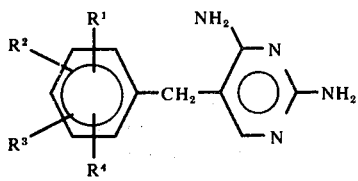

wherein $R^1$, $R^2$, $R^3$ and $R^4$ are the same or different and can each be a hydrogen atom, a halogen atom, an alkyl group, an alkoxy group or a benzyloxy group or, when $R^1$, and $R^2$ are each hydrogen atoms, $R^3$ and $R^4$ taken together can be a methylene dioxy group substantially all of the particles of potentiator in the suspension having a largest dimension less than $50\mu m$, in an aqueous solution of a pharmaceutically acceptable water soluble salt of a sulphonamide with a strong base, and wherein the pH of the preparation is in the range of from 9.75 to 12.0.

2. An aqueous injectable preparation as claimed in claim 1 wherein the pH of the preparation is equal to or greater than 10.

3. An aqueous injectable preparation as claimed in claim 1 wherein the pH of the preparation is in the range from 10 to 10.5.

4. An aqueous injectable preparation, as claimed in claim 1, which comprises a suspension of a finely divided potentiator selected from the group consisting of trimethoprim; diaveridine; 2,4-diamino-5-(3,4,6-trimethoxy benzyl)pyrimidine; 2,4-diamino-5-(4-chlorobenzyl)-6-ethylpyrimidine; ormetoprim; 2,4-diamino-5-(3,4-dimethoxy-5-bromobenzyl)pyrimidine and pyrimethamine, substantially all of the particles of the potentiator in the suspension having a largest diameter less than $50\mu m$, in an aqueous solution of a pharmaceutically acceptable water soluble salt of a sulphonamide selected from the group consisting of sulphadiazine; sulphadoxine; sulphadimethoxine, sulphamethoxazole; sulphaquinoxaline and sulphadimidine, with a strong base.

5. An aqueous injectable preparation as claimed in claim 1 wherein the sulphonamide is of general formula:

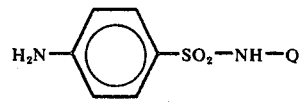

wherein Q is a substituted or unsubstituted pyrimidin-2-yl or 4-yl group or is a substituted isoxazolyl group.

6. An aqueous injectable preparation as claimed in claim 1 wherein 90% of the particles by number have a largest dimension less than $20\mu m$.

7. An aqueous injectable preparation as claimed in claim 1 wherein at least 95% by number of the particles have a largest dimension less than $20\mu m$.

8. An aqueous injectable preparation as claimed in claim 1 wherein at least 99% of the particles have a largest dimension less than $20\mu m$.

9. An aqueous injectable preparation as claimed in claim 1 wherein at least 99.5% of the particles have a largest dimension less than $5\mu m$.

10. An aqueous injectable preparation as claimed in claim 1 wherein the pharmaceutically acceptable salt of the sulphonamide is a sodium salt.

11. An aqueous injectable preparation as claimed in claim 1 wherein the ratio of sulphonamide to potentiator by weight is from 20:1 to 0.1:1.

12. An aqueous injectable preparation as claimed in claim 1 containing up to 84% w/v of medicaments.

13. An aqueous injectable preparation as claimed in claim 1 which additionally contains a non-ionic wetting agent.

14. A method of treating bacterial infections in birds or mammals other than humans which comprises subcutaneously or intramuscularly injecting an effective dosage of the preparation claimed in claim 1 into the bird or mammal.

15. The preparation of claim 11 in which the potentiator is trimethoprim and the sulphonamide is sulphadoxine.

16. The preparation of claim 11 in which the potentiator is trimethoprim and the sulphonamide is sulphadiazine.

17. The preparation of claim 11 in which the potentiator is trimethoprim and the sulphonamide is sulphamethoxazole.

* * * * *